(12) United States Patent
Drown et al.

(10) Patent No.: US 12,201,356 B2
(45) Date of Patent: Jan. 21, 2025

(54) DUAL WAVELENGTH LASER ABLATION SYSTEMS FOR MRI-GUIDED ABLATION PROCEDURES AND RELATED DEVICES AND METHODS

(71) Applicant: Medtronic Navigation, Inc., Louisville, CO (US)

(72) Inventors: Christine Drown, Louisville, CO (US); Rebecca Vincelette, Louisville, CO (US); Roopali Shah, Louisville, CO (US); Nicole Barney, Louisville, CO (US); Benjamin Ewing, Louisville, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 159 days.

(21) Appl. No.: 17/246,174

(22) Filed: Apr. 30, 2021

(65) Prior Publication Data

US 2021/0338328 A1    Nov. 4, 2021

Related U.S. Application Data

(60) Provisional application No. 63/019,810, filed on May 4, 2020.

(51) Int. Cl.
*A61B 18/20* (2006.01)
*A61B 17/00* (2006.01)
*A61B 18/00* (2006.01)
*A61B 18/22* (2006.01)
*A61B 34/20* (2016.01)

(52) U.S. Cl.
CPC .............. *A61B 18/20* (2013.01); *A61B 18/22* (2013.01); *A61B 2017/0023* (2013.01); *A61B 2018/00005* (2013.01); *A61B 2018/00577* (2013.01); *A61B 2018/00642* (2013.01); *A61B 2018/00702* (2013.01); *A61B 2018/00791* (2013.01); *A61B 2018/207* (2013.01); *A61B 2034/2051* (2016.02)

(58) Field of Classification Search
CPC .. A61B 2034/2051; A61B 18/20; A61B 18/22
See application file for complete search history.

(56) References Cited

U.S. PATENT DOCUMENTS 6,056,741 A    5/2000   Van Saarloos
8,876,810 B2   11/2014  Neuberger
(Continued)

FOREIGN PATENT DOCUMENTS

| EP | 1958584    | 8/2008  |
|----|------------|---------|
| WO | 2008153999 | 12/2008 |
| WO | 2018115410 | 6/2018  |

OTHER PUBLICATIONS

International Search Report and Written Opinion dated Aug. 16, 2021 for PCT/US2021/030292.

*Primary Examiner* — Mallika D Fairchild
*Assistant Examiner* — Thien Jason Tran
(74) *Attorney, Agent, or Firm* — Sheridan Ross P.C.

(57) ABSTRACT

Laser ablation devices and related systems and methods may have laser outputs with multiple wavelengths. Laser ablation devices may include a laser energy source that can emit two or more laser outputs with different wavelengths. Some laser ablation devices include a processor to control the laser energy source to cause the laser energy source to emit a target wavelength blend with the laser outputs.

20 Claims, 7 Drawing Sheets

(56) References Cited

U.S. PATENT DOCUMENTS

| | | | |
|---|---|---|---|
| 10,251,703 B2 | 4/2019 | Albeck et al. | |
| 10,285,758 B2 | 5/2019 | Rink et al. | |
| 2006/0116669 A1* | 6/2006 | Dolleris | A61B 18/203 606/17 |
| 2009/0248004 A1 | 10/2009 | Altshuler et al. | |
| 2012/0232534 A1* | 9/2012 | Rink | A61B 18/24 606/3 |
| 2013/0190742 A1 | 7/2013 | Connors et al. | |
| 2014/0147802 A1 | 5/2014 | Naldoni | |
| 2015/0182283 A1 | 7/2015 | Boutoussov | |
| 2018/0140866 A1 | 5/2018 | Daly et al. | |
| 2018/0214204 A1* | 8/2018 | Karmarkar | A61B 5/0507 |
| 2018/0310988 A1* | 11/2018 | Panescu | A61B 5/6843 |

* cited by examiner

DUAL WAVELENGTH LASER ABLATION SYSTEMS FOR MRI-GUIDED ABLATION PROCEDURES AND RELATED DEVICES AND METHODS

RELATED APPLICATION

This application claims priority to U.S. Provisional Application No. 63/019,810, filed on May 4, 2020 and titled, "Dual Wavelength Laser Ablation Systems for MRI-Guided Ablation Procedures and Related Devices and Methods," which is hereby incorporated by reference in its entirety.

TECHNICAL FIELD

The present disclosure related generally to the field of medical devices. More particularly, some embodiments related to laser tumor ablation devices and related systems and methods.

BRIEF DESCRIPTION OF THE DRAWINGS

The written disclosure herein describes illustrative embodiments that are non-limiting and non-exhaustive. Reference is made to certain of such illustrative embodiments that are depicted in the figures.

DETAILED DESCRIPTION

Figure 1:
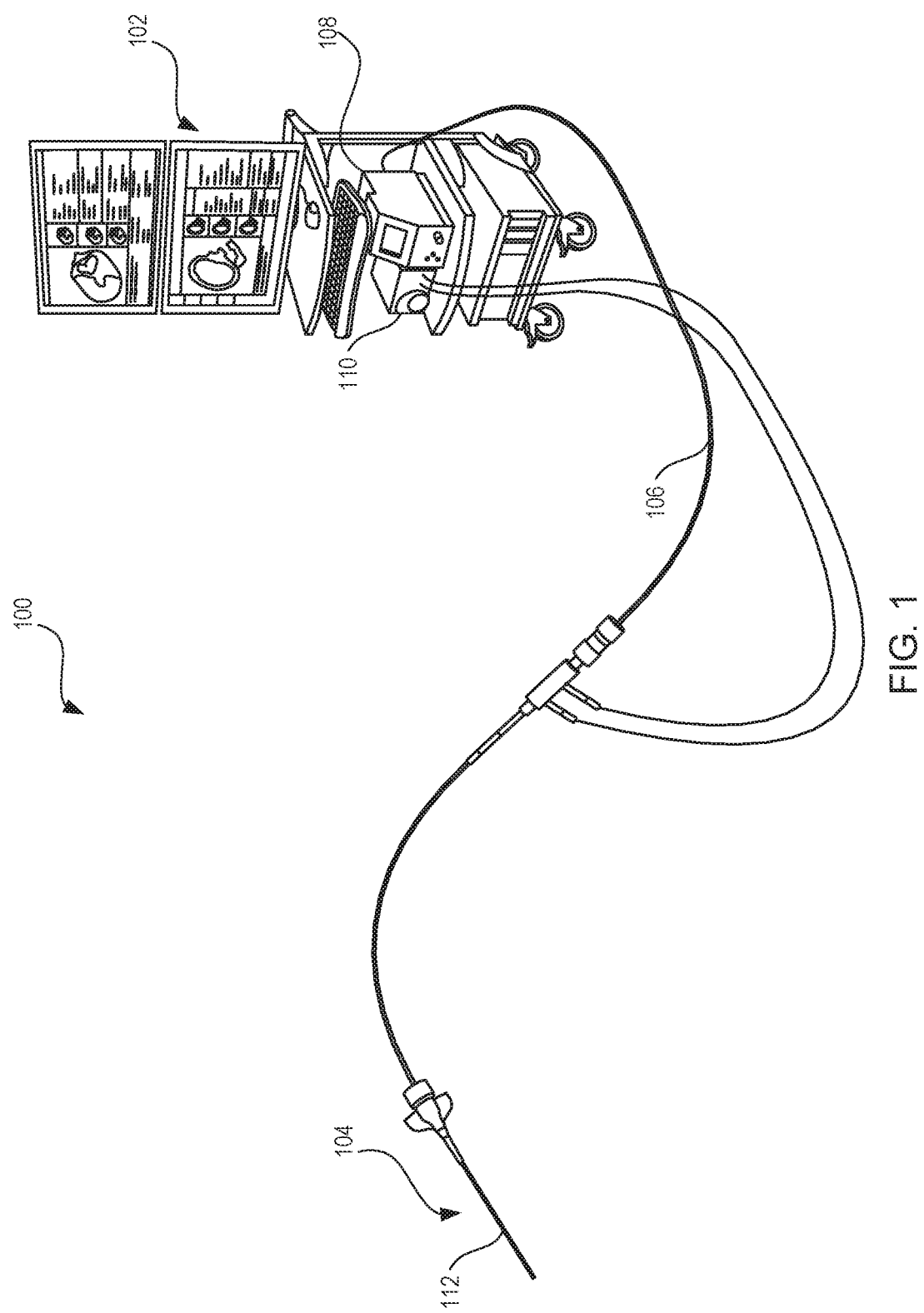
FIG. 1 is a perspective view of a tumor ablation system that includes a base unit, a remote, and a medical device.

Laser interstitial thermal therapy (LITT) is a technique for treating various tumors in the liver, brain, or abdominal locations, as well as for treating benign alterations, such as prostate adenomas. A laser applicator is inserted into a desired region of treatment to deliver laser energy. After positioning of the laser applicator, a laser output is emitted to irradiate target tissue and generate heat that leads to thermal tissue necrosis. Thus, LITT may be used to ablate a tumor via thermal energy generated from the laser output while limiting side effects or additional damage to surrounding structures.

Typically, the laser output used for LITT is limited to a single wavelength. Various wavelengths heat and penetrate tissue differently. For example, a smaller wavelength penetrates the tissue less than a larger wavelength. The smaller wavelength heats the tissue faster with steeper temperature gradients from a center of the lesion outward. Thus, the smaller wavelength provides fast ablation with minimal thermal damage to surrounding tissue. However, the smaller wavelength is better suited to create a smaller lesion. The larger wavelength penetrates the tissue farther than the smaller wavelength. The larger wavelength heats the tissue more gradually than the smaller wavelength and features shallower temperature gradients from the center of the lesion outward. The larger wavelength is better suited for creating larger lesions. However, the shallower temperature gradients result in less delineated boundaries of the ablation lesion. A laser ablation system limited to a single wavelength chosen during production will be restricted to the advantages as well as the disadvantages of the single wavelength.

The systems, methods, and apparatuses described herein incorporate multiple wavelengths to create a wide variety of lesion sizes. Using multiple wavelengths allows for a tumor ablation system to more precisely create smaller lesions while still being capable of treating larger areas. For example, in some embodiments, the laser ablation system may be capable of operating with a wavelength of 980 nm and 1064 nm. The 980 nm wavelength may be used for creating medium lesions while the 1064 nm wavelength may be used for creating large lesions. In some embodiments, the laser ablation system may be capable of emitting laser outputs with more than two wavelengths (e.g., 800 nm, 980 nm, and 1064 nm). The multi-wavelength laser system allows users to customize the lesion in the patient, enabling them to achieve both large and small lesions.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

While specific wavelengths are mentioned throughout the specification, it should be understood that the exact wavelength may be used as well as wavelengths around the exact wavelength. Thus, when reference is made to a laser output with a laser wavelength of 980 nm, the application is referencing a wavelength of exactly or about 980 nm.

The phrase "coupled to" is broad enough to refer to any suitable coupling or other form of interaction between two or more entities. Two components may be coupled to each other even though they are not in direct contact with each other. For example, two components may be coupled to one another through an intermediate component. The phrases "attached to" and "attached directly to" refer to interaction between two or more entities that are in direct contact with each other and/or are separated from each other only by a fastener of any suitable variety (e.g., an adhesive).

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

FIG. 1 is a perspective view of a laser ablation system 100. The laser ablation system 100 may be used in one or more medical procedures, such as procedures to treat a brain tumor. The laser ablation system 100 however is not limited to treating brain tumors, but may be used to treat tumors in various other locations in the body. The laser ablation system 100 may comprise a base unit 102 and a laser applicator 104.

The base unit 102 may comprise a laser energy source 108 that provides two or more laser outputs with different wavelengths to the laser applicator 104 through a laser fiber 106. In some embodiments, two or more laser outputs have wavelengths between 800 nm and 1310 nm. For example, in some embodiments, the two or more laser outputs comprise a first laser output with a wavelength of 980 nm and a second laser output with a wavelength of 1064 nm. In some embodiments, the two or more laser outputs further comprise a third laser output with a wavelength of 800 nm.

The laser energy source 108 may emit the laser outputs independently of each other. For example, the laser energy source 108 may emit a laser output with a wavelength of 980 nm and not emit a laser output with a wavelength of 1064 nm. In some embodiments, the laser energy source 108 may emit the different laser outputs simultaneously. In some embodiments, the laser energy source 108 may cycle between the different laser outputs such that only one laser output is emitted at a time.

The laser energy source 108 may emit the laser outputs using various techniques. In some embodiments, the laser energy source 108 may emit a pulsed laser. In some embodiments, the laser energy source 108 may emit a continuous laser output. In some embodiments, the laser energy source 108 may flicker a continuous laser output on and off to manage laser delivery to a surgical target.

The laser applicator 104 is coupled to the laser energy source 108 through the laser fiber 106. The laser applicator 104 outputs laser radiation at an ablation site. The laser applicator 104 may comprise a distal portion of the laser fiber 106 inserted into a cooling catheter 112. The laser fiber 106 may terminate in a diffusing tip. The diffusing tip may diffuse and emit the laser output in a radial pattern. In some embodiments, the diffusing tip may be optimized to diffuse one of the wavelengths of the laser outputs. In some embodiments, the diffusing tip may be optimized to diffuse an average wavelength of the wavelengths that the laser energy source 108 is capable of emitting. In some embodiments, the laser ablation system 100 may comprise multiple laser fibers, each optimized to diffuse a wavelength that the laser energy source 108 is capable of emitting.

The cooling catheter 112 may cool the diffusing tip, the laser fiber 106, and tissue adjacent the diffusing tip. In the illustrated embodiment, during delivery of energy a cooling medium is pumped through the cooling catheter 112 such that it flows through a fluid inlet lumen around and in contact with the distal portion of the laser fiber 106 and diffusing tip. The cooling medium exits through a fluid outlet lumen. The cooling medium flows from the outlet lumen and through a cooling unit 110. The cooling unit 110 comprises a pump to circulate the cooling medium and a heat exchanger. The heat exchanger cools the cooling medium, and the cooling medium then travels back to the fluid inlet lumen of the cooling catheter 112.

Accordingly, both the tissue under treatment and the laser applicator 104 are cooled, minimizing the possibility of damaging the laser applicator 104 or overheating adjacent tissue. The cooling may allow for increased deposition of photon energy by reducing or eliminating damage of tissue in direct contact with the laser applicator 104.

In some embodiments, the temperature or flow rate of the cooling medium may be controlled to provide a desired cooling of tissue or the laser applicator 104. For example, the base unit 102 may adjust the cooling based on one or more of the current wavelength being output by the laser energy source 108, the power delivered by each laser energy source, tissue temperature, and laser applicator 104 temperature. The cooling medium may flow in a continuous or in an intermittent manner.

Examples of a cooling medium include room temperature and chilled fluids including liquids and gases such as saline solution, water, air, nitrogen, carbon dioxide, alcohols, and other suitable substances. Suitable substances include fluids with a suitable heat capacity or that are transmissive to the wavelength of light emitted from the laser applicator 104. In some embodiments, the fluid may also include sealants, coagulants, anti-coagulants, anesthetics, optical agents, radio-opaque agents, dyes, magnetic resonance agents, therapeutic drugs, and chemotherapy agents, among other treatment agents.

The base unit 102 may further include a processor to control which laser output wavelength is emitted or what combination of laser outlets is emitted. For example, the base unit 102 may determine a blend of the two or more laser outputs to apply thermal energy across the ablation site based on one or more of a chosen laser power, tissue temperature, laser applicator 104 temperature, progress of ablation, temperature thresholds, target thermal radiation pattern, size of the ablation site, shape of the ablation site, type of disposable used, target pathology, and tissue parameters.

Blending laser outputs includes emitting laser energy using a combination of wavelengths where each wavelength delivers a target amount of power. Accordingly, a blended laser output comprises a set of wavelengths with a corresponding set of target powers. The blended laser output may define parameters for continuous wave or pulsed lasers to achieve the target amount of power delivered by each wavelength. The parameters may include pulse widths, pulse rates, and duty cycles of the respective laser beams.

Figure 2:
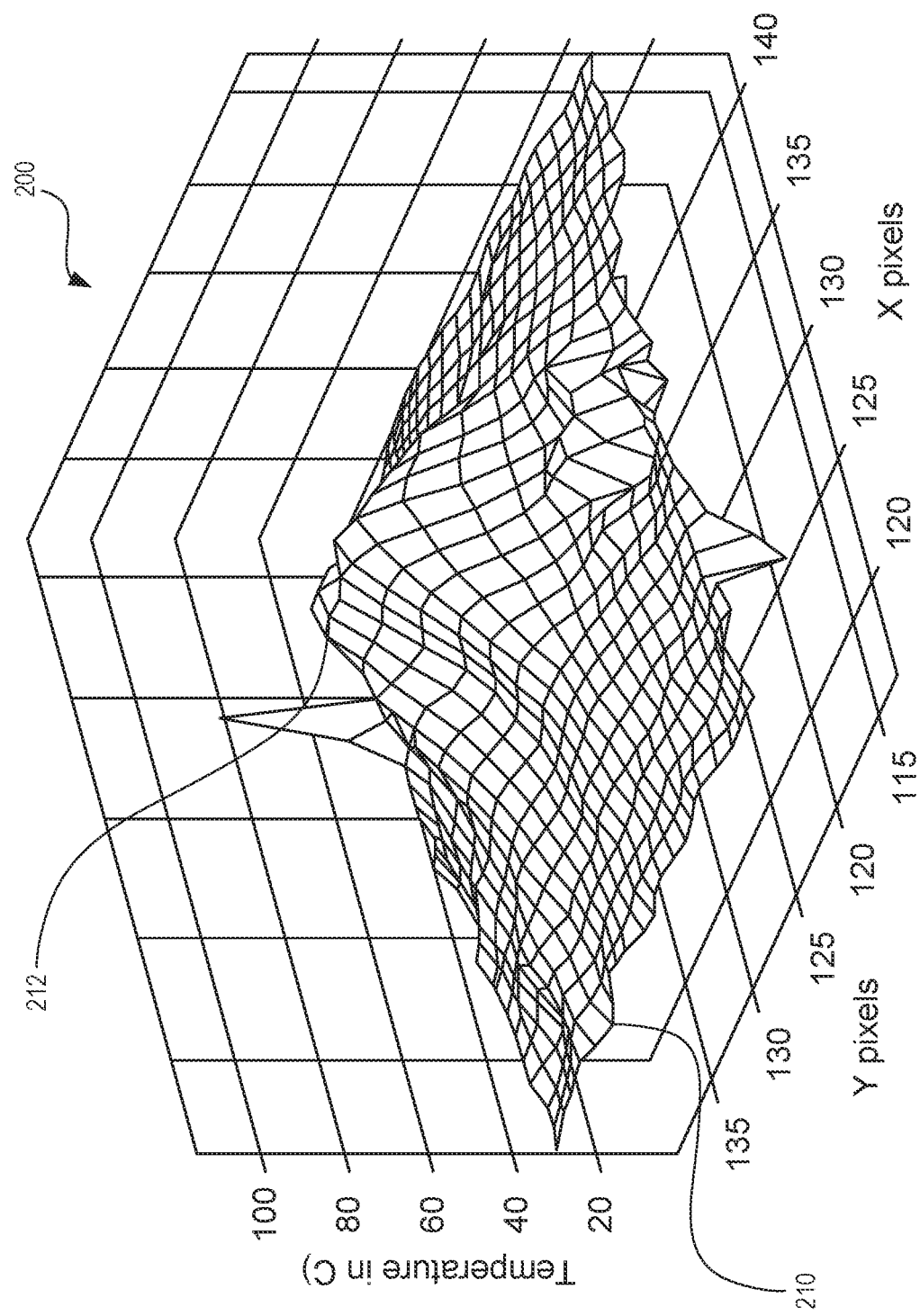
FIG. 2 is a graph of a thermal distribution corresponding to a laser output with a 980 nm wavelength.

FIG. 2 is a graph 200 of a thermal distribution 210 corresponding to a laser output with a 980 nm wavelength. The 980 nm wavelength laser penetrates tissue less than a larger wavelength laser. The smaller penetration causes the energy to get absorbed by a smaller amount of tissue, resulting in heating a center 212 of an ablation zone quickly. Also, as can be seen the temperature gradient steeply slopes down from the center 212, resulting in a crisp transition between dead tissue and alive tissue. The 980 nm wavelength laser performs well for medium and small lesions. However, when used for large lesions additional power is required, causing the center to become very hot and possibly resulting in undesirable conditions such as cavitation, voids, and charring.

Figure 3:
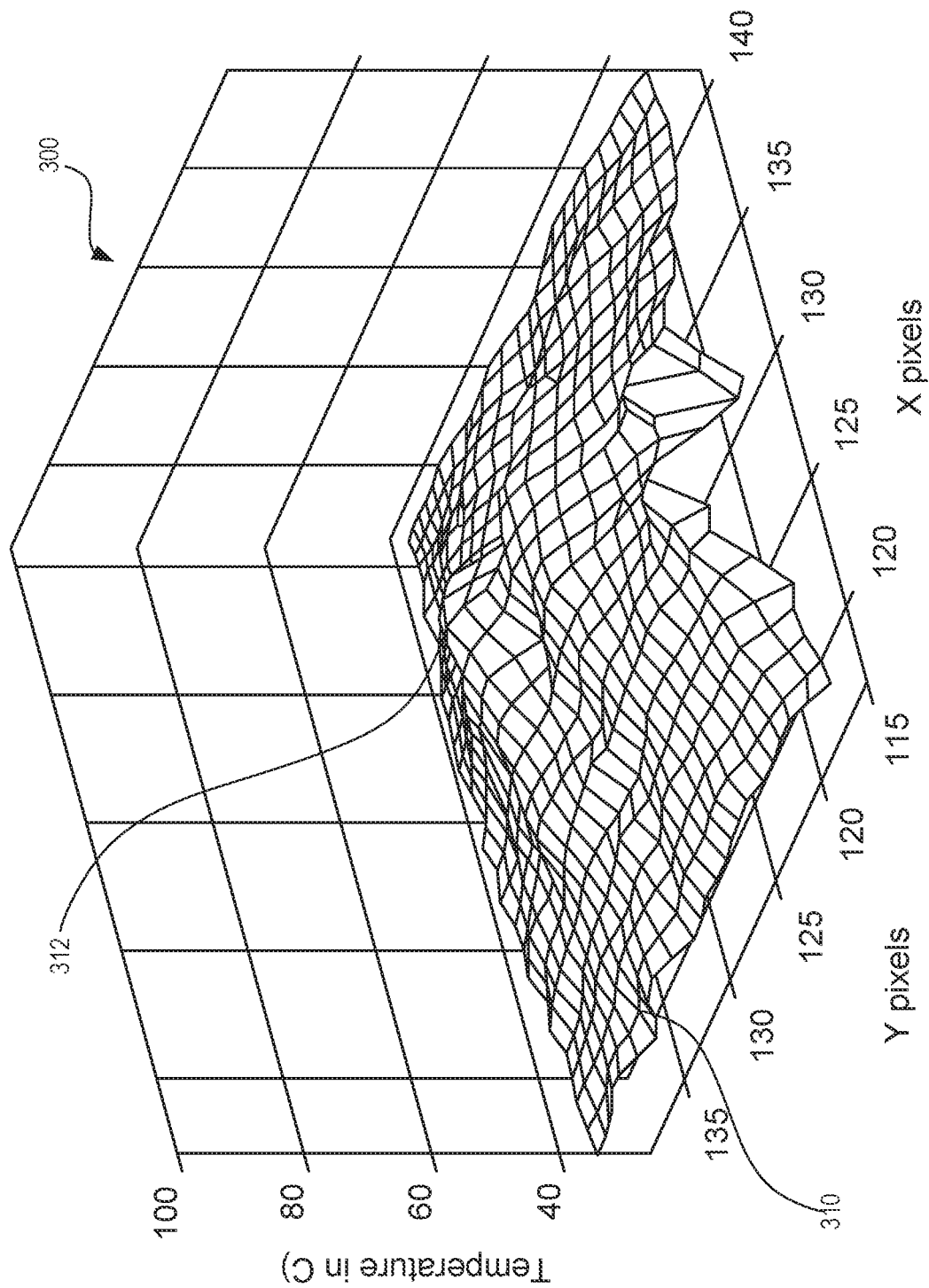
FIG. 3 is a graph of a thermal distribution corresponding to a laser output with a 1064 nm wavelength.

FIG. 3 is a graph 300 of a thermal distribution 310 corresponding to a laser output with a 1064 nm wavelength. The 1064 nm wavelength laser penetrates further into tissue than the 980 nm wavelength laser shown in FIG. 2. Thus, the 1064 nm wavelength laser is able to heat up larger lesions than the 980 nm wavelength laser.

However, the thermal distribution 310 does illustrate a few potentially undesirable aspects of using a 1064 nm wavelength laser. As shown, a center 312 of the thermal distribution 310 for the 1064 nm wavelength is not as hot as the 980 nm wavelength laser. Therefore, the ablation time must be increased to generate an equivalent thermal dose. Additionally, the temperature gradient is a gradual slope down from the center 312, resulting in less delineated ablation lesions.

A system may use multiple wavelength lasers (e.g., both the 980 nm wavelength laser and the 1064 nm wavelength laser) to create various size ablation lesions while limiting undesirable aspects of the different wavelengths. For example, a 980 nm wavelength laser may be used for a small lesion and a 1064 nm wavelength may be used for a large lesion.

Figure 4:
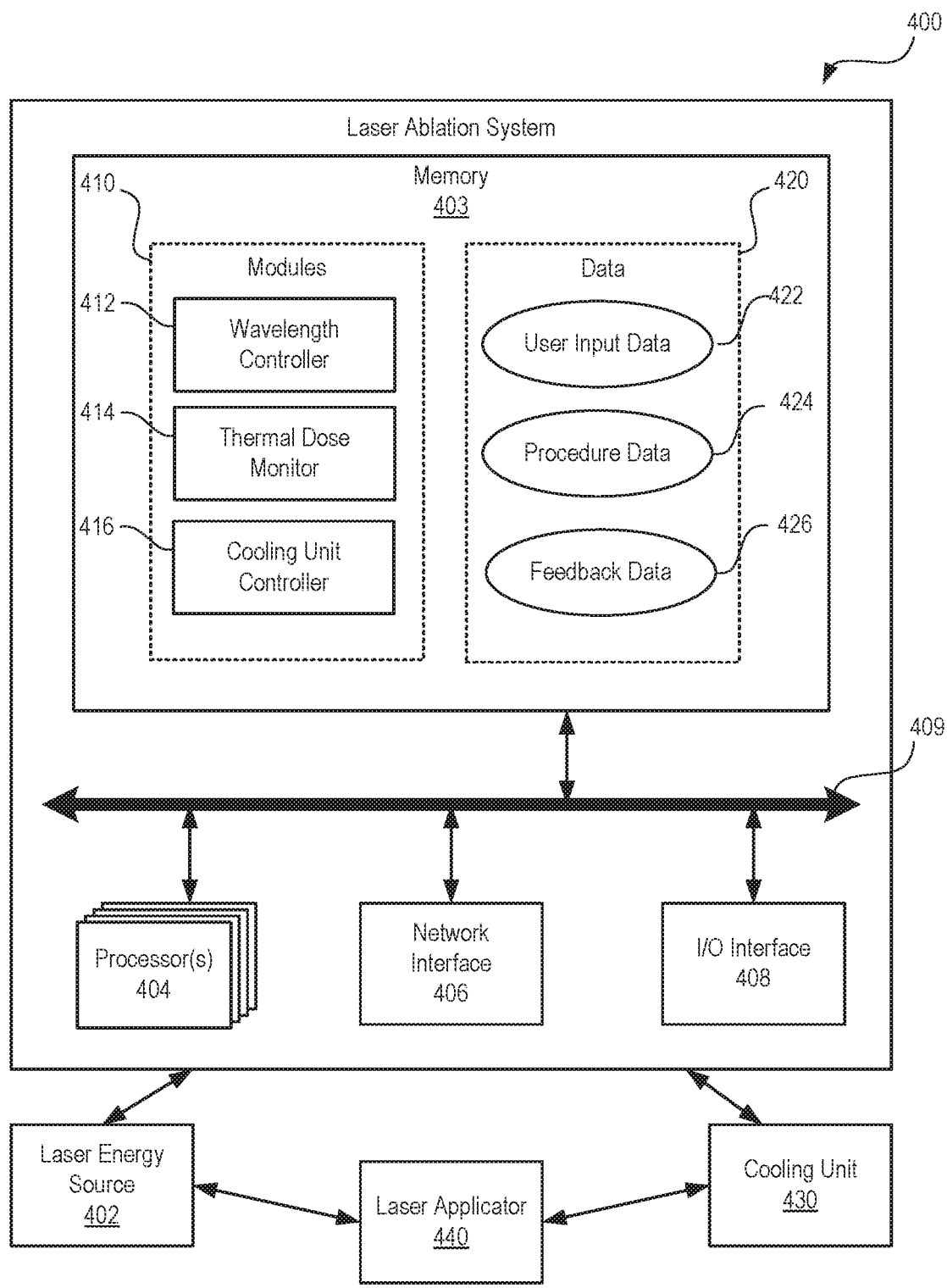
FIG. 4 is a block diagram of a laser ablation system coupled to a laser applicator, according to one embodiment.

FIG. 4 is a block diagram of a laser ablation system 400 in communication with a laser applicator 440 according to one embodiment. The laser ablation system 400 may be the same laser ablation system illustrated in FIG. 1.

The laser ablation system 400 controls a laser energy source 402 that can produce laser outputs at two or more wavelengths to output to the laser applicator 440. The laser energy source 402 may include multiple laser outputs with different wavelengths. The laser output can be transmitted between the laser energy source 402 and the laser applicator 440 over a laser fiber. The laser energy is emitted from the laser applicator 440 to penetrate into the tissue and be converted into thermal energy via tissue heating within a desired ablation region. The laser ablation system 400 controls the laser energy source to modulate power output at the two or more wavelengths based on several factors including user input data 422, procedure data 424, and feedback data 436.

In some embodiments, the laser ablation system 400 controls a cooling unit 430 to cool the laser applicator 440. The laser output can be transmitted between the laser energy source 402 and the laser applicator 440 over a laser fiber. The laser ablation system 400 may control the cooling to modulate the amount of cooling based on the wavelengths generated by the laser energy source 402. In some embodiments, the laser ablation system 400 may control the amount of cooling based on an amount of power output at each of the two or more wavelengths.

In some embodiments, the laser applicator 440 may comprise a distal portion of the laser fiber inserted into a cooling catheter 112. The laser fiber may terminate in a diffusing tip. In some embodiments, the laser fiber and the diffusing tip may be optimized for one of the wavelengths that is output by the laser energy source 402 or optimized for a wavelength between the range of wavelengths that is output by the laser energy source 402. In some embodiments, multiple laser fibers and diffusing tips may be used with each optimized for a different wavelength.

The laser ablation system 400 can include a memory 403, one or more processors 404, a network interface 406, an input/output interface 408, and a system bus 409.

The one or more processors 404 may include one or more general purpose devices, such as an Intel®, AMD®, or other standard microprocessor. The one or more processors 404 may include a special purpose processing device, such as ASIC, SoC, SiP, FPGA, PAL, PLA, FPLA, PLD, or other customized or programmable device. The one or more processors 404 can perform distributed (e.g., parallel) processing to execute or otherwise implement functionalities of the presently disclosed embodiments. The one or more processors 404 may run a standard operating system and perform standard operating system functions. It is recognized that any standard operating systems may be used, such as, for example, Microsoft® Windows®, Apple® MacOS®, Disk Operating System (DOS), UNIX, IRJX, Solaris, SunOS, FreeBSD, Linux®, ffiM® OS/2® operating systems, and so forth.

The memory 403 may include static RAM, dynamic RAM, flash memory, one or more flip-flops, ROM, CD-ROM, DVD, disk, tape, or magnetic, optical, or other computer storage medium. The memory 403 may include a plurality of program modules 410 and program data 420. The memory 403 may be local to the laser ablation system 400, as shown, or may be distributed and/or remote relative to the laser ablation system 400.

The memory 403 may include the data 420. Data generated or used by the laser ablation system 400, such as by the program modules 410 or other modules, may be stored on the memory 403, for example, as stored program data 420.

The data 420 may be organized as one or more databases. The data 420 may include user input data 422, procedure data 424, and feedback data 426.

The user input data 422 may be entered by a user through the input/output interface 408. In some embodiments, the user input data 422 may identify one or more of surgical goals, thermal gradients, and temperatures. The user input data 422 may include maximum temperature that a physician wants to reach in target areas, areas the physician wants to protect from thermal damage, and areas the physician wants to damage.

The user input data 422 may include at least one of a wavelength, a target lesion size, a protected structure location, pathology information, target temperature thresholds (e.g., a maximum threshold and a minimum threshold), a target thermal dose, a target time at the target temperature threshold, a target output power, or other user-defined parameters. For example, the user could define temperature goals (e.g., a minimum threshold and maximum thresholds) across an image, and the laser ablation system 400 could determine an appropriate laser wavelength blend to obtain the desired results.

In some embodiments, the user input data 422 may include a desired wavelength. For example, the user may choose a laser wavelength from a list of two or more wavelengths to use during the ablation. If the user specifies a laser wavelength, the laser ablation system 400 may use the chosen laser wavelength without blending it with other laser wavelengths.

In some embodiments, the user input data 422 may include information regarding the area of the target lesion. For example, the user input data 422 may include a target lesion size. In some embodiments, the user input data 422 may also indicate areas to not ablate (protected areas). In some embodiments, the user input data 422 may also include a degree of protection for the protected areas.

In some embodiments, the user input data 422 may include equipment used during surgery. For example, the user input data 422 may indicate a laser applicator that will be used for the procedure.

In some embodiments, the user input data 422 may identify more specific information about the target lesion. For example, the user input data 422 may include pathology information of the target tissue. Additionally, the user input data 422 may also include a target thermal dose. The target thermal dose represents the desired thermal dose to be delivered to an identified area. The target thermal dose may be set to a value that to cause ablation or the target thermal dose may be set to a value below the ablation point to prime the area for other surgeries, drug deliveries, or therapies. For example, the user may identify targets to open a blood brain barrier with thermal insult rather than applying thermal necrosis.

The procedure data 424 may comprise information regarding pathology and treatments. For example, the procedure data 424 may include typical tissue response to a laser with a certain wavelength.

The feedback data 426 may include an image of the tissue, thermal data of the ablation zone, and correlation information between the image and the thermal data. The image may be a magnetic resonance imaging scan. The thermal data may include temperature near a catheter as determined by MRI thermometry or a temperature probe. In some embodiments, the thermal data may include temperatures across the image of the tissue. The feedback data 426 may also include progress of ablation towards a surgical target.

In some embodiments, the feedback data 426 may also include results of a test low power dose of laser energy. While the procedure data 424 may provide a typical tissue response to a laser with a certain wavelength, the feedback data 426 that includes results of a test dose may provide accurate local tissue response.

The program modules 410 may include all or portions of other elements of the laser ablation system 400. The program modules 410 may run multiple operations concurrently or in parallel by or on the one or more processors 404. In some embodiments, portions of the disclosed modules, components, and/or facilities are embodied as executable instructions embodied in hardware or firmware, or stored on a non-transitory, machine-readable storage medium. The executable instructions may comprise computer program code that, when executed by a processor and/or computing device, cause a computing system to implement certain processing steps, procedures, and/or operations, as disclosed herein. The modules, components, and/or facilities disclosed herein may be implemented and/or embodied as a driver, a library, an interface, an API, FPGA configuration data, firmware (e.g., stored on an EEPROM), and/or the like. In some embodiments, portions of the modules, components, and/or facilities disclosed herein are embodied as machine components, such as general and/or application-specific devices, including, but not limited to: circuits, integrated circuits, processing components, interface components, hardware controller(s), storage controller(s), programmable hardware, FPGAs, ASICs, and/or the like. Accordingly, the modules disclosed herein may be referred to as controllers, layers, services, engines, facilities, drivers, circuits, subsystems, and/or the like. The modules 410 may comprise a wavelength controller 412, a thermal dose monitor 414, and a cooling unit controller 416.

The thermal dose monitor 414 monitors temperature and progress to a surgical goal. The thermal dose monitor 414 may monitor temperature at the ablation site, in protected areas, and across other points of an image. The thermal dose monitor 414 may determine the temperature using MRI thermometry or a temperature probe. Additionally, the thermal dose monitor 414 may calculate a thermal dose delivered and determine if thermal insult or thermal necrosis has occurred. Thermal dose represents the accumulated thermal energy that the tissue in that location was subjected to during the total time of the procedure. The thermal dose monitor 414 may output data to be stored as feedback data 426.

The wavelength controller 412 may use one or more of the user input data 422, the procedure data 424, and the feedback data 426 to monitor an ablation site and control a laser output with a particular wavelength or multiple laser outputs with a blend of wavelengths emitted by the laser energy source 402.

The laser outputs may have wavelengths between 800 nm and 1310 nm. For example, in some embodiments, the wavelength controller 412 may control a laser energy source with a first laser output with a wavelength of 980 nm and a second laser output with a wavelength of 1064 nm. In some embodiments the wavelength controller 412 may control a laser energy source with a first laser output with a wavelength of 980 nm, a second laser output with a wavelength of 1064 nm, and a third laser output with a wavelength of 800 nm.

The wavelength controller 412 may choose which particular wavelength or blend of wavelengths should be emitted by the laser energy source 402 based on user input data 422. For example, if a user directly selects the wavelength to be used, the wavelength controller 412 causes the laser energy source 402 to emit the selected wavelength.

In some embodiments, the wavelength controller 412 may determine the wavelength or wavelength blend based on one or both of a desired lesion size and shape. For example, for a larger lesion the wavelength controller 412 will select a larger wavelength or a wavelength blend comprising a larger portion of power delivered by the larger wavelength. For a smaller lesion the wavelength controller 412 will select a smaller wavelength or a wavelength blend comprising a larger portion of power delivered by the smaller wavelength.

In some embodiments, the wavelength controller 412 may determine the wavelength or wavelength blend based on the disposable used. For example, if the laser applicator 440 is more efficient for a first wavelength and less efficient for a second wavelength, the wavelength controller 412 may increase the power delivered at the second wavelength to obtain a desired amount of power delivered at each of the wavelengths.

In some embodiments, the wavelength controller 412 may determine a wavelength based on the chosen laser power. For example, a wavelength blend for a chosen laser power may comprise 70% power delivered by a laser output with a 1064 nm wavelength and 30% power delivered by a laser output with a 980 nm wavelength.

Additionally, the wavelengths selected may be based on a combination of user input data 422, procedure data 424, and feedback data 426. For example, the wavelength controller 412 may pick the wavelength picked based on a desired lesion size combined with what is not to be ablated, and/or pathology information.

The procedure data 424 may be used by the wavelength controller 412 to establish an initial wavelength blend selection. For example, the wavelength controller 412 may prescribe a blend based on the target pathology or tissue parameters.

In some embodiments, the wavelength controller 412 may determine a wavelength blend based on the type of procedure to be performed. For example, some procedures may only require thermal insult while other procedures are to apply thermal critical damage to the tissue. The wavelength controller 412 may receive user input indicating a surgical target, the surgical target comprising a larger area and a smaller area within the larger area. The wavelength controller 412 may cause the laser energy source 402 to emit a first laser output with a first wavelength, the first laser output delivering sufficient power to cause sub-critical damage to the larger area and emit a second laser output with a second wavelength, and the second laser output delivering sufficient power to cause necrosis to the smaller area.

Thus, the wavelength controller 412 may use one wavelength to deliver sub-critical damage (e.g., low level of thermal insult) and a second wavelength to deliver critical damage. For example, the sub-critical wavelength could be used to open a blood brain barrier and allow drugs or an immune response to access this region of the brain. This wavelength would not be intended to cause necrosis but rather combined with another wavelength such that there is damage in the center of the ablation zone and broader thermal insult surrounding the center.

The wavelength controller 412 may use the feedback data 426 to determine adjustments the output of the laser energy source 402. For example, the wavelength controller 412 could determine a prescribed wavelength blend based on the results of an initial low power dose test of laser energy. To administer the low power dose test, the wavelength controller 412 could turn on a low power test dose. The wavelength controller 412 could determine a blend of the two or more laser outputs to apply thermal energy across the ablation site based on a thermal response of tissue at the ablation site to the test dose, and based on the thermal response of the tissue (as monitored on MRI thermometry or by a thermal probe) select an appropriate blend of wavelengths. The low power dose test may also be used by a physician to manually adjust the wavelength blend.

In some embodiments, the wavelength controller 412 uses the feedback data 426 as a feedback loop during a procedure to adjust the wavelength blend. The feedback loop could incorporate some or all of temperature near the laser applicator 440 (as determined by MRI thermometry or a temperature probe in the disposable), progress of ablation towards a user-defined surgical target, and user-defined temperatures. For example, the user could define temperature goals, minimum thresholds, and maximum thresholds across an image, and the wavelength controller 412 could determine the appropriate blend to attempt to achieve those surgical targets. As another example, the wavelength controller 412 could cause the laser energy source 402 to emit a greater amount of larger wavelength laser output than a smaller wavelength laser output when a center part of the ablation site approaches a maximum target temperature before an outer part of the ablation site reaches a minimum target temperature.

The wavelength controller 412 may use a number of techniques to manage the amount of power delivered at each wavelength. For example, in some embodiments the laser outputs with different wavelengths are all emitted simultaneously at different or equal power.

In some embodiments, the wavelength controller 412 may emit the laser outputs for different amounts of time to deliver a target power delivered over a period of time. For example, a first laser output may have a duty cycle that is longer than a second laser output. In some embodiments, the wavelength controller 412 may cause the laser energy source to alternate pulses of each wavelength. For example, a first wavelength could be cycled on and off then a second wavelength 2 could be cycled on and off. The amount of time each are left on may provide the tissue with the intended blend between the two. For example, over a period of time the first wavelength may be left on twice as long as the second wavelength to obtain a 66%/33% blend between the wavelengths. The overall speed of the pulsing may be shorter than the thermal relaxation time of the tissue so that the tissue would experience the pulses as a continuous wave blend.

In some embodiments, the wavelength controller 412 may cause the laser energy source 402 to pulse each wavelength at the same time. Each wavelength could be turned on and off to control the effective power output of each wavelength individually. However, the laser outputs with different wavelengths would be allowed to both be on at the same time. Depending on the fraction of time that each wavelength is on, the wavelength controller 412 would be able to generate the appropriate blend. For example, if wavelength 1 is on 100% of the time but wavelength 2 is only on 50% of the time, the wavelength controller 412 again obtains a 66%/33% blend.

In some embodiments, each laser output wavelength could be turned on independently for longer timescales (i.e., timescales longer than the thermal relaxation time of the tissue, so that the tissue has time to respond independently to each wavelength). Using the longer timescales, the wavelength controller 412 could monitor the reaction of each wavelength. The wavelength controller 412 could use the reaction of the tissue to determine adjust the power, duration, or selection of the next laser output wavelength. Using the longer timescales, the wavelength controller 412 may also cause thermal insult to a broad area with one wavelength and then use a different wavelength to cause thermal necroses to a smaller area. In some embodiments, the wavelength controller 412 uses longer timescales to achieve temperature thresholds in phases with different wavelengths.

The cooling unit controller 416 controls the cooling unit 430 to adjust an amount of cooling for the laser applicator 440. The cooling unit controller 416 may adjust the amount of cooling based on a ratio of power delivered at each wavelength. For example, the cooling unit controller 416 may increase or decrease the amount of saline flowing through the laser applicator 440 based on the wavelength blend.

The input/output interface 408 may facilitate user interaction with one or more input devices and/or one or more output devices. The input device(s) may include a keyboard, mouse, touchscreen, light pen, tablet, microphone, sensor, or other hardware with accompanying firmware and/or software. The output device(s) may include a monitor or other display, printer, speech or text synthesizer, switch, signal line, or other hardware with accompanying firmware and/or software. For example, in one embodiment, the input/output interface 408 comprises a display to provide a graphical user interface (GUI) illustrating the potential ablation perimeters. The input/output interface 408 can receive the user input data 422. In some embodiments, the input/output interface 408 is a touchscreen, and the size input is received via the touchscreen. In some embodiments, the input/output interface 408 can superimpose the target ablation perimeters on an image of the tissue.

The network interface 406 may facilitate communication with other computing devices and/or networks and/or other computing and/or communications networks. The network interface 406 may be equipped with conventional network connectivity, such as, for example, Ethernet (IEEE 1102.3), Token Ring (IEEE 1102.5), Fiber Distributed Datalink Interface (FDDI), or Asynchronous Transfer Mode (ATM). Further, the network interface 406 may be configured to support a variety of network protocols such as, for example, Internet Protocol (IP), Transfer Control Protocol (TCP), Network File System over UDP/TCP, Server Message Block (SMB), Microsoft® Common Internet File System (CIFS), Hypertext Transfer Protocols (HTTP), Direct Access File System (DAFS), File Transfer Protocol (FTP), Real-Time Publish Subscribe (RTPS), Open Systems Interconnection (OSI) protocols, Simple Mail Transfer Protocol (SMTP), Secure Shell (SSH), Secure Socket Layer (SSL), and so forth.

The system bus 409 may facilitate communication and/or interaction between the other components of the laser ablation system 400, including the one or more processors 404, the memory 403, the input/output interface 408, and the network interface 406.

Figure 5:
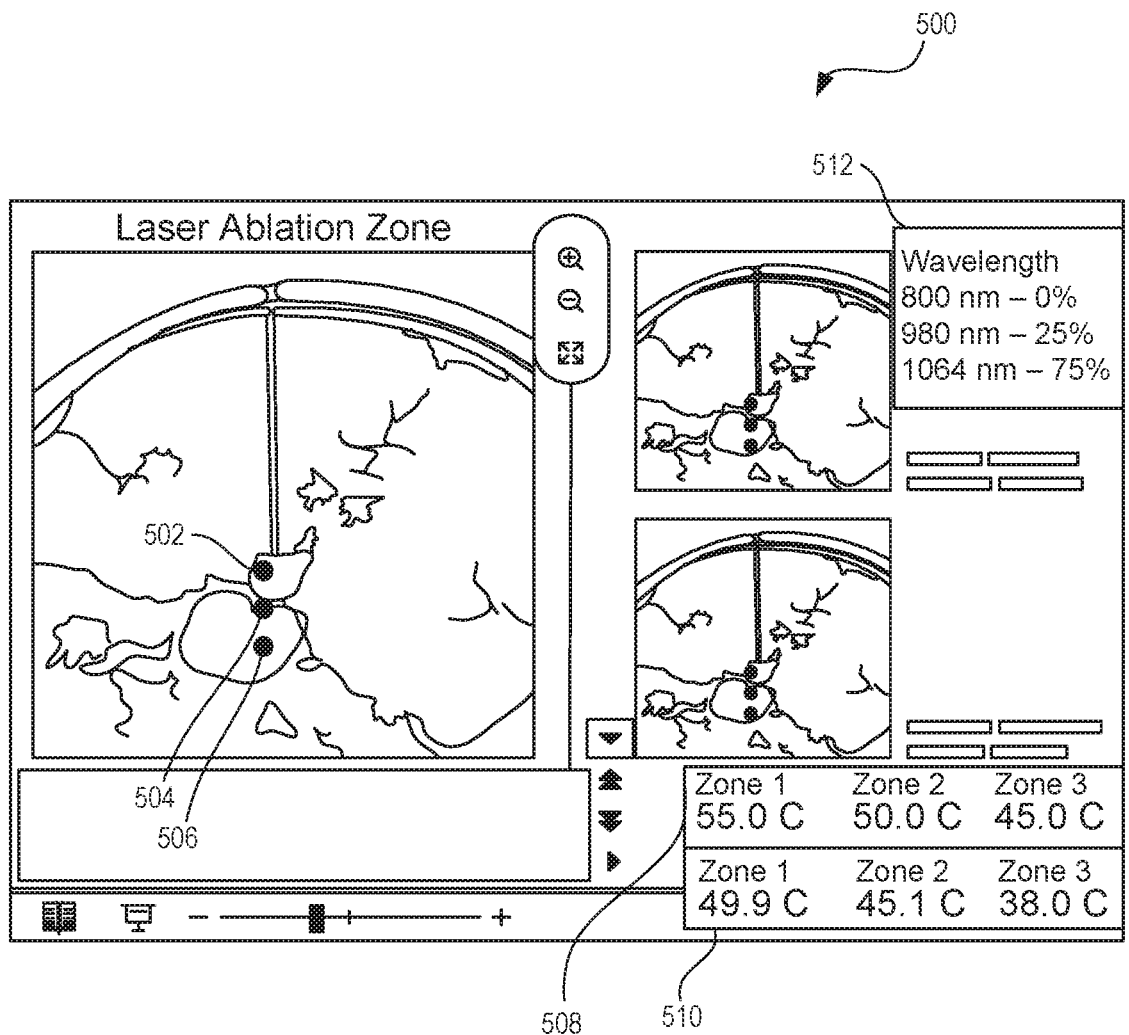
FIG. 5 is a graphical user interface (GUI) that may be displayed by the laser ablation system of FIG. 4, according to one embodiment.

FIG. 5 is a GUI 500 that may be displayed by the laser ablation system 400 of FIG. 4. A user may interact with the GUI 500 to identify the tissue zones (e.g., first tissue zone 502, second tissue zone 504, and third tissue zone 506), thermal gradients, temperature thresholds 508, and surgical goals. In some embodiments, the GUI 500 may also allow a user to enter pathology information.

The tissue zones (e.g., first tissue zone 502, second tissue zone 504, and third tissue zone 506) may be used to mark target ablation zones or protected areas. The tissue zones marked as target ablation zones identify the tissue to be ablated, while the tissue zones marked as protected areas identify tissue to be preserved. The tissue zones may be entered by the user as points on an image or may be contours outlining the zones.

In the illustrated embodiment, the temperature thresholds 508 represent minimum temperatures for the tissue zones. In other embodiments, a user may enter a maximum threshold for each zone.

In some embodiments, a target thermal dose a user wants to deliver to tissue zones may be received by the GUI 500. For example, the target thermal dose may indicate a thermal dose for priming for other surgeries, drugs, and therapies. In some embodiments, the GUI 500 may receive a value indicating a degree of protection that the user wants to achieve in protected areas. In some embodiments, the GUI 500 may receive a value indicating targets where the user wants to open the blood brain barrier via thermal insult.

The GUI 500 may also display feedback data 510. The feedback data 510 may indicate progress to a surgical goal. In the illustrated embodiment, the feedback data 510 indicates a measured temperature for each tissue zone.

In some embodiments, the GUI 500 may also display the current wavelength blend 512. A user may directly select the wavelengths, or the GUI 500 may populate the current wavelength blend 512 when the laser ablation system determines a wavelength blend based on one or more of user input, procedure data, and feedback data.

Figure 6:
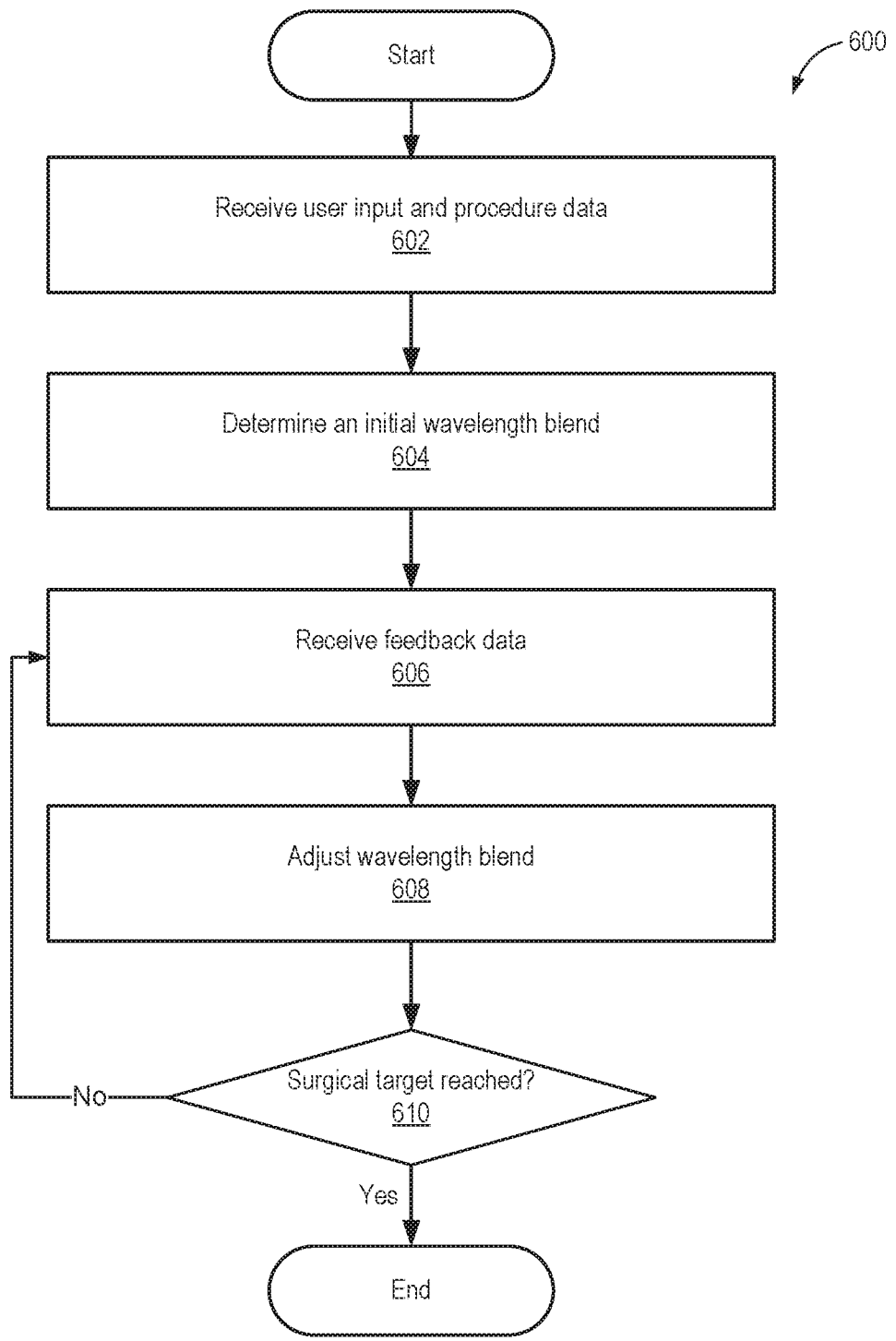
FIG. 6 is a flow chart of a method for controlling a wavelength blend to deliver laser energy to target tissue, according to one embodiment.

FIG. 6 is a flow chart of a method 600 for controlling a wavelength blend to deliver laser energy to target tissue, according to one embodiment. The method may be implemented by a laser ablation system such as the laser ablation system 400 of FIG. 4.

The laser ablation system may receive 602 user input and procedure data. The user input may include a surgical target that comprises one or more of surgical goals, thermal gradients, a desired wavelength, a desired wavelength blend, a target lesion size, a protected structure location, pathology information, target temperature thresholds (e.g., a maximum threshold and a minimum threshold), a target thermal dose, a target time at the target temperature threshold, a target output power, pathology, and other user-defined parameters. The procedure data may comprise information regarding pathology and treatments When implanting the method 600 the laser ablation system may further determine 604 an initial wavelength blend based on the user input and procedure data. For example, the laser ablation system may use a laser with a larger wavelength when the user input identifies a large lesion.

The method 600 further comprises receiving 606 feedback data. The feedback data may include an image of the tissue, thermal data of the ablation zone, and progress of ablation towards a surgical target. The system may adjust 608 the wavelength blend based on the feedback data. For example, as the temperature in a center of a lesion increases faster than an external portion of the lesion, the amount of power delivered by a small wavelength within the wavelength blend may be reduced.

The method 600 further comprises determining 610 if the surgical target has been reached. The surgical target may be a target thermal dose for an area, a target temperature for an area, thermal necrosis for an ablation area, or an amount of thermal insult delivered to an area. If the surgical target is not reached, a laser ablation system would receive 606 feedback data again and adjust 608 the wavelength blend based on the additional feedback.

Figure 7:
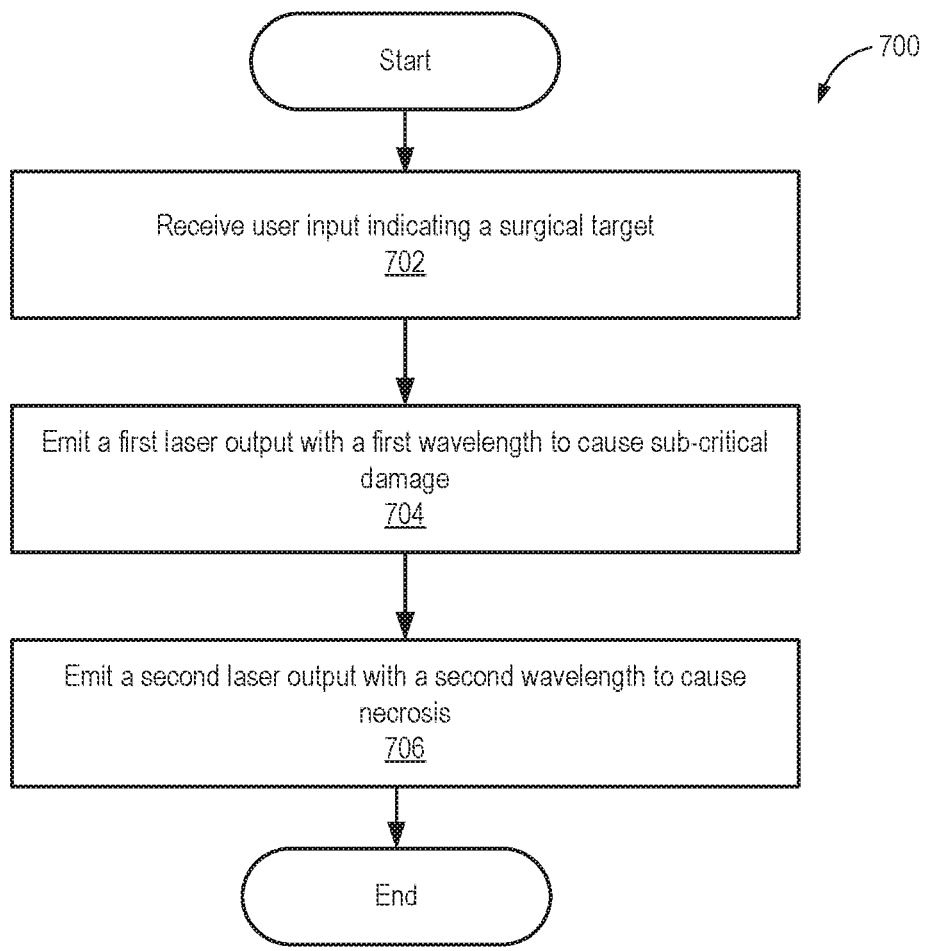
FIG. 7 is a flow chart of a method for tissue ablation, according to one embodiment.

FIG. 7 is a flow chart of a method 700 for tissue ablation, according to one embodiment. The method may be implemented by a laser ablation system such as the laser ablation system 400 of FIG. 4. A system using this method 700 may receive 702 user input indicating a surgical target, the surgical target comprising a first area and a second area. The first area may be a larger area than the second area.

In some situations, a physician may desire to deliver a sub-critical thermal dose to a larger area and a critical thermal dose to a smaller area. The system may emit 704 a first laser output with a first wavelength. The first laser output may deliver sufficient power to cause sub-critical damage to the first area. The system may also emit 706 a second laser output with a second wavelength, the second laser output delivering sufficient power to cause necrosis to the second area.

The first laser output may have a larger wavelength than the second laser output. For example, the first laser output may have a wavelength of 1064 nm and the second laser output may have a wavelength of 980 nm. The laser output with the larger wavelength may be used for thermal insult across a broader area, while the laser output with the smaller wavelength may deliver sufficient power to cause thermal necrosis to a smaller area.

The first and second laser outputs may be emitted simultaneously or in stages. For example, the laser output with the larger wavelength may deliver a first target thermal energy to the larger area first and then the laser output with the smaller wavelength may deliver a second target thermal energy to the smaller area.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to an "embodiment" means that a particular feature, structure, or characteristic described in connection with that embodiment is included in at least one embodiment. Thus, references to embodiments throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A laser ablation system comprising:
a laser energy source configured to emit two or more laser outputs with different wavelengths;
a laser applicator coupled to the laser energy source via a laser fiber, the laser applicator to output laser radiation at a tissue of an ablation site; and
a processor to:
monitor temperatures across tissue zones of the tissue at the ablation site, the tissue zones of the tissue at the ablation site comprising a target ablation zone and a protected area tissue zone, wherein the target ablation zone comprises a target tissue to be ablated, and wherein the protected area tissue zone comprises tissue that is not to be ablated; and
control the laser energy source to emit at least one laser output of the two or more laser outputs to apply thermal energy across the ablation site using the different wavelengths, wherein emitted laser outputs are chosen based on a wavelength and current monitored temperatures across each of the tissue zones of the tissue at the ablation site.

2. The laser ablation system of claim 1, wherein the two or more laser outputs comprise a first laser output with a wavelength of 980 nm and a second laser output with a wavelength of 1064 nm.

3. The laser ablation system of claim 2, wherein the processor causes the laser energy source to emit a greater amount of the second laser output than the first laser output when a center part of the tissue at the ablation site approaches a maximum target temperature before an outer part of the tissue at the ablation site reaches a minimum target temperature.

4. The laser ablation system of claim 2, wherein the two or more laser outputs further comprise a third laser output with a wavelength of 800 nm.

5. The laser ablation system of claim 1, wherein the two or more laser outputs have wavelengths between 800 nm and 1310 nm.

6. The laser ablation system of claim 1, wherein the processor is further to determine a blend of the two or more laser outputs to apply thermal energy across the ablation site based on the current monitored temperatures across each of the tissue zones of the tissue at the ablation site.

7. The laser ablation system of claim 1, wherein the processor is further to cause the laser energy source to:
emit an initial low power dose of laser energy; and
determine a blend of the two or more laser outputs to apply thermal energy across the ablation site based on a thermal response of the tissue at the ablation site to the initial low power dose of laser energy emitted.

8. The laser ablation system of claim 1, wherein the processor is further to choose the emitted laser outputs based on a target lesion size and feedback received during a procedure, the feedback comprising at least one of a progress of ablation towards a surgical target and a target thermal radiation pattern.

9. The laser ablation system of claim 1, wherein the two or more laser outputs comprise a first laser output with a first wavelength and a second laser output with a second wavelength, wherein the processor causes the laser energy source to emit the first laser output in on and off pulses having a first duty cycle and emit the second laser output in on and off pulses having a second duty cycle.

10. The laser ablation system of claim 9, wherein the first duty cycle is longer than the second duty cycle.

11. The laser ablation system of claim 9, wherein the processor causes the laser energy source to emit the on and off pulses having the first duty cycle alternatively to the on and off pulses having the second duty cycle.

12. The laser ablation system of claim 11, wherein the processor causes the laser energy source to:
monitor a reaction of the tissue at the ablation site in response to emission of the first laser output at the first wavelength and the second laser output at the second wavelength; and
adjust at least one of a power, duration, and selection of a next laser output wavelength based on the reaction monitored.

13. The laser ablation system of claim 12, wherein the reaction of the tissue at the ablation site is a thermal relaxation time of the tissue at the ablation site.

14. A laser ablation method, comprising:
inserting a laser applicator into a desired region of treatment comprising a tissue of an ablation site;
emitting, by a laser energy source configured to emit two or more laser outputs with different wavelengths, a laser energy to apply thermal energy at the tissue of the ablation site;
monitoring, by a processor, temperatures across tissue zones of the tissue at the ablation site, the tissue zones of the tissue at the ablation site comprising a target ablation zone and a protected area tissue zone, wherein the target ablation zone comprises a target tissue to be ablated, and wherein the protected area tissue zone comprises tissue that is not to be ablated; and
controlling, by the processor, the laser energy source to emit at least one laser output of the two or more laser outputs to apply thermal energy across the ablation site using the different wavelengths, wherein the at least one laser output emitted is chosen based on a wavelength and current monitored temperatures across each of the tissue zones of the tissue at the ablation site.

15. The laser ablation method of claim 14, wherein the two or more laser outputs comprise a first laser output with a wavelength of 980 nm and a second laser output with a wavelength of 1064 nm.

16. The laser ablation method of claim 15, further comprising:
controlling, by the processor, the laser energy source to emit a greater amount of the second laser output than the first laser output when a center part of the tissue at the ablation site approaches a maximum target temperature before an outer part of the tissue at the ablation site reaches a minimum target temperature.

17. The laser ablation method of claim 14, wherein prior to emitting the laser energy, the laser ablation method further comprises:
causing, by the processor, the laser energy source to emit an initial low power dose of laser energy; and
determining, by the processor and based on a thermal response of the tissue at the ablation site to the initial low power dose of laser energy, a blend of the two or more laser outputs to apply the thermal energy across the ablation site.

18. A non-transitory computer-readable medium including instructions that when executed by one or more processors of a tissue ablation system cause the tissue ablation system to:
monitor temperatures across tissue zones of tissue at an ablation site, the tissue zones of the tissue at the ablation site comprising a target ablation zone and a protected area tissue zone, wherein the target ablation zone comprises a target tissue to be ablated, and wherein the protected area tissue zone comprises tissue that is not to be ablated; and control a laser energy source that is configured to emit two or more laser outputs with different wavelengths to emit, from a laser applicator coupled to the laser energy source, at least one laser output of the two or more laser outputs to apply thermal energy across the ablation site using the different wavelengths, wherein the at least one laser output emitted is chosen based on a wavelength and current monitored temperatures across each of the tissue zones of the tissue at the ablation site.

19. The non-transitory computer-readable medium including instructions of claim 18, wherein the instructions are further to cause the tissue ablation system to cause the laser energy source to emit a greater amount of a second laser output of the two or more laser outputs than a first laser output of the two or more laser outputs when a center part of the tissue at the ablation site approaches a maximum target temperature before an outer part of the tissue at the ablation site reaches a minimum target temperature, and wherein the first laser output comprises a wavelength of 980 nm and the second laser output comprises a wavelength of 1064 nm.

20. The non-transitory computer-readable medium including instructions of claim 18, wherein prior to the instructions are further to cause the tissue ablation system to:

emit an initial low power dose of laser energy; and determine a blend of the two or more laser outputs to apply thermal energy across the ablation site based on a thermal response of the tissue at the ablation site to the initial low power dose of laser energy emitted.

* * * * *